United States Patent [19]

Miyoshi et al.

[11] Patent Number: 4,760,023

[45] Date of Patent: Jul. 26, 1988

[54] [21-LEUCINE] HUMAN UROGASTRONE, CORRESPONDING GENE, CORRESPONDING RECOMBINANT PLASMID, TRANSFORMED CELL AND PROCESS FOR PRODUCTION THEREOF

[75] Inventors: Kenichi Miyoshi; Shinichiro Sumi; Akira Hasegawa; Masanori Suzuki, all of Hiroshima, Japan

[73] Assignee: Wakunaga Seiyaku Kabushiki Kaisha, Osaka, Japan

[21] Appl. No.: 627,533

[22] Filed: Jul. 3, 1984

[30] Foreign Application Priority Data

Jul. 8, 1983 [JP] Japan .................................. 58-123520

[51] Int. Cl.⁴ ...................... C12N 15/00; C12N 1/20; C07H 15/12; C07K 7/10; C07K 7/30
[52] U.S. Cl. .................................. 435/172.3; 435/320; 435/253; 536/27; 530/309; 530/324; 935/10; 935/13; 935/27; 935/73
[58] Field of Search ..................... 435/68, 70, 172.3; 935/9, 10, 11, 27, 29, 56, 60, 73; 530/309, 324, 334, 339; 536/27

[56] References Cited

PUBLICATIONS

Urdea et al., 1983, Proc. Natl. Acad. Sci., U.S.A., 80:7461–7465.
Stryer, L., 1975, pp. 18–19, In: Biochemistry, W. H. Freeman and Co.: San Francisco.
Smith et al., 1982, Chemical Synthesis and Cloning of a Gene for Human B-Urogastrone, Nucleic Acids Research 10 (15): 4467–4482.
Itakura et al., 1977, Expression in Eschenchia Coli of a Chemically Synthesized Gene for the Hormone Somatostatin, Science 198:1056–1063.
Banks et al., 1983–Chem. Abstr. 100 (21): #169364r.
Sumi et al., 1985, Chem. Abstr. 103 (9): #60035s.

Primary Examiner—Charles F. Warren
Assistant Examiner—David T. Fox
Attorney, Agent, or Firm—Oblon, Fisher, Spivak, McClelland & Maier

[57] ABSTRACT

[21-Leucine] human urogastrone, hUG, comprising a polypeptide represented by the specified amino acid sequence has been found to be equivalent to the known hUG which has 21-Met and is disclosed together with its syntheses. Double-stranded polydeoxyribonucleotides comprising a structural gene for expressing the hUG, a recombinant plasmid comprising a structural gene for expressing the hUG, and E. coli transformed by the recombinant plasmid are also disclosed. Thanks to the substitution of Met in the known hUG by Leu, the peptide of hUG can now be produced by a conventional or typical method in which a genetically engineered precursor fused polypeptide is cleaved by cyanogen bromide at Met in the fused polypeptide.

6 Claims, 4 Drawing Sheets

[21-LEUCINE] HUMAN UROGASTRONE, CORRESPONDING GENE, CORRESPONDING RECOMBINANT PLASMID, TRANSFORMED CELL AND PROCESS FOR PRODUCTION THEREOF

BACKGROUND OF THE INVENTION

1. Field of the Invention

The present invention relates to [21-leucine] human urogastrone (often referred to as "[21-L] hUG" hereinafter) and a process for the production of [21-L] hUG by genetic engineering. More specifically, the present invention further includes a chemically synthesized structural gene for [21-L] hUG, a corresponding recombinant plasmid and a transformed cell.

2. Discussion of the Backgrond

Human urogastrone (hUG) is a peptide comprising 53 amino acid residues and having an action of inhibiting gastric acid secretion, which was discovered in human urine by Gregory et al in 1975 [Nature, 257, 325 (1975)].

hUG is a polypeptide having the following structure and contains three disulfide bonds in the molecule:

> H-Asn-Ser-Asp-Ser-Glu-Cys-Pro-Leu-Ser-His-Asp-
> Gly-Tyr-Cys-Leu-His-Asp-Gly-Val-Cys-Met-
> Tyr-Ile-Glu-Ala-Leu-Asp-Lys-Tyr-Ala-Cys-Asn-
> Cys-Val-Val-Gly-Tyr-Ile-Gly-Glu-Arg-Cys-Gln-
> Tyr-Arg-Asp-Leu-Lys-Trp-Trp-Glu-Leu-Arg-
> OH

In the same year, Cohen et al discovered a human epidermal growth factor (hEGF), which is a growth factor promoting proliferation and keratinization of the epithelial tissue, in human urine and isolated and purified this factor [Proc. Natl. Acad. Sci. USA, 72, 1317 (1975)]. The entire amino acid structure of hEGF has not been elucidated, but according to recent researches on the basis of gel electrophoretic analysis and receptor competition with mouse epidermal growth factor (mEGF), it is now considered that hEGF and hUG are identical.

It is now confirmed that hUG and hEGF have common physiological actions [Ann. Rev. Biochem., 48, 193 (1979)]. Furthermore, by comparison in view of the physiological actions of hUG with mEGF having the same 37 amino acid residues as those of hUG among the 53 amino acid residues and three S-S bonds at the same positions as in hUG, the activity of hUG/hEGF or mEGF has been found beyond species, and it is therefore considered that these physiological actions are due to the specific stable three-dimensional structure involved.

However, this hUG (hEGF) is isolated only in a minute amount from human urine, and mass production has been desired. Recent developments in genetic engineering have produced excellent results in the production of heterologous proteins by E.coli or the like. Accordingly, application of this technique to the mass production of hUG is naturally considered and has already been proposed (Japanese Patent Application Laid-Open Specification No. 122096/82).

As one most effective method for synthesizing peptides according to the genetic engineering process, mention can be made of a process in which: a gene coding for an intended peptide is linked to a structural gene for another protein derived from a host (such as β-galactosidase or TrpE of E. coli through AUG (a codon for methionine) and is cloned in the host; the biosynthesized, so-called fused protein is treated with cyanogen bromide; and the intended peptide is recovered (Japanese Patent Application Laid-Open Specifications No.84603/81 and No.145221/81). However, synthesis of a peptide containing Met cannot be performed according to this process. Since hUG contains Met as its 21st amino acid residue from the N-terminus, the above process cannot be applied directly to synthesis of hUG. For example, the above mentioned laid-open specification (Japanese Patent Application Laid-Open Specification No.122096/82) discloses a process in which by utilizing a trypsin-insensitive property of hUG, the objective peptide is produced in the form of a fused protein having Lys-Lys attached upstream of the N-terminus and the intended peptide is recovered by trypsin treatment. However, according to another report [Journal of Japanese Medical Association, 85, 833 (1981)], the activity of hUG is lost if five amino acids of hUG are removed from the C-terminus. Accordingly, it is doubtful whether or not hUG is cleaved at the desired point. Therefore, it is not deemed that this process will be advantageous.

Based on the supposition that the 21st amino acid residue, namely, Met, of hUG does not participate in the physiological activity of hUG, we conducted research and confirmed that when Met is substituted by Leu (leucine) having a similar structure so that a conventional cyanogen bromide treatment of a fused protein is applicable, the recovered [21-L] hUG has an activity equivalent to the activity of hUG (hEGF). The present invention is based on this and other findings.

Although it has been clarified that the activity of hUG (hEGF) depends on the three-dimensional structure having three disulfide bonds, its specific active site and mechanism of its action are not clear at present. Accordingly, the above technical concept is not believed obvious to those skilled in the art.

SUMMARY OF THE INVENTION

The present invention is based on the confirmed findings: that a structural gene representing an hUG derivative in which the 21st amino acid residue comprises Leu which is not Met, that is, [21-L] hUG, can be chemically synthesized; that this structural gene can be inserted into an appropriate plasmid; that transformation of an appropriate host cell by this recombinant plasmid and production and recovery of [21-L] hUG by culturing of the transformed cell are possible; and that the formed [21-L] hUG has an activity similar to the activity of hUG (hEGF).

Accordingly, [21-L] hUG of the present invention is characterized in that it comprises a polypeptide represented by the following amino acid sequence formula:

> H-Asn-Ser-Asp-Ser-Glu-Cys-Pro-Leu-Ser-His-Asp-
> Gly-Tyr-Cys-Leu-His-Asp-Gly-Val-Cys-Met-
> Tyr-Ile-Glu-Ala-Leu-Asp-Lys-Tyr-Ala-Cys-Asn-
> Cys-Val-Val-Gly-Tyr-Ile-Gly-Glu-Arg-Cys-Gln-
> Tyr-Arg-Asp-Leu-Lys-Trp-Trp-Glu-Leu-Arg-
> OH

It should be understood that this structure is expressed as a primary structure for convenience's sake.

The process for the production of [21-L] hUG according to the present invention comprises the steps of (1) chemically synthesizing a structural gene of [21-leucine] human urogastrone corresponding to a polypeptide in which the 21st amino acid of human urogastrone is leucine, (2) inserting this gene into a plasmid vegetative in a selected host cell to form a recombinant plasmid vegetative in the host cell, (3) causing transformation of the host cell by the plasmid, and (4) culturing the transformed cell and recovering the formed [21-leucine] human urogastrone.

A typical example of the plasmid vegetative in the host cell is a plasmid capable of utilizing the expression system of a lactose operon, and a typical example of the origin of the lactose operon expression system and the host cell used for transformation is E. coli belonging to the genus Escherichia.

Furthermore, the present invention also includes a duplex (i.e. a pair of complementary strands of) polydeoxyribonucleotide containing a structural gene capable of compressing [21-L] hUG, a recombinant plasmid comprising said structural gene, and E. coli transformed by the recombinant plasmid.

The problems encountered in the extraction and purification of natural hUG (hEGF) can be overcome by using the extracts of the cloned cells as the starting substance according to the present invention.

The process of the present invention suggests that the scope of application of one of the most effective methods of recovering an intended peptide from a so-called fused protein biosynthesized by the genetic engineering process can be broadened by utilizing a treatment with cyanogen bromide.

DETAILED DESCRIPTION OF THE INVENTION

[21-Leucine] Human Urogastrone

[21-L] hUG of the present invention is a polypeptide represented by the following amino acid sequence formula:

H-Asn-Ser-Asp-Ser-Glu-Cys-Pro-Leu-Ser-His-Asp-
Gly-Tyr-Cys-Leu-His-Asp-Gly-Val-Cys-Met-
Tyr-Ile-Glu-Ala-Leu-Asp-Lys-Tyr-Ala-Cys-Asn-
Cys-Val-Val-Gly-Tyr-Ile-Gly-Glu-Arg-Cys-Gln-
Tyr-Arg-Asp-Leu-Lys-Trp-Trp-Glu-Leu-Arg-
OH

In the above formula, Asn and other symbols represent amino acids such as aspargine, as recognized in the art.

This polypeptide is the same as hUG except that the 21st amino acid is Leu.

In the above formula, [21-L] hUG is expressed as a primary structure for convenience's sake. Strictly speaking, in [21-L] hUG of the present invention, there are present disulfide bonds between the 6th Cys and 20th Cys, the 14th Cys and 31st Cys, and the 33rd Cys and 42nd Cys.

[21-L] hUG has physiological activities equivalent to those of hUG (hEGF), such as inhibition of stomach ulceration and cell proliferation promoting activity. Accordingly, [21-L] hUG can be used as a counterpart of hUG.

Production of [21-L] Human Urogastrone

(1) Structural Gene

(1) Designing of Gene

The base sequence of hUG gene is not known.

Accordingly, several codons satisfying the following conditions are selected among codons designating the amino acids constituting this peptide and are used for synthesis of DNA.

(i) The region rich in A-T base pairs is not subsequent to the region rich in G-C base pairs.

(ii) None of synthetic fragments described hereinafter have an undesirable complementary base sequence in the molecule or intermolecularly.

It is preferable that this structural gene be so designed that at least one restriction site necessary for facilitating verification of transformants or base substitutions by replacement of appropriate fragments with other fragments of base substitutions so that one can examine the relationship between the structure of hUG and its activity is contained, and an undesirable restriction site is not contained. In the case of [21-L] hUG, it is preferable that base sequences for recognition of restriction enzymes EcoRI, HinfI, AluI, RsaI and BglII be formed. It is also preferable that codons used frequently in the host be selected and used.

Accordingly, a preferred example of the structural gene of [21-L] hUG used in the present invention has base sequences shown in the Experiment and Gene Design Diagram described hereinafter. Needless to say, in the diagram, this structural gene is a portion ranging from AAT corresponding to N-terminal Asn to CGT corresponding to C-terminal Arg).

The process for expression of this structural gene is described in detail, for example, in Japanese Patent Application Laid-Open Specification No.92696/79. When a lactose operon derived from E. coli is used for expression of this gene, it is preferable that this gene be inserted in the recognition site of restriction enzyme EcoRI locating in the z-gene of the lactose operon, and the gene be expressed in the form of a protein fused with β-galactosidase. That is, the codon ATG of Met to be attacked by cyanogen bromide is linked to the 5'-terminus of the structural gene, and at least one stop codon is located at the 3'-terminus. Then, if necessary, appropriate base sequences are flanked by ATG for coordination with a frame beginning with the initiation codon of the β-galactosidase, and base sequences to be inserted into the site for recognition of EcoRI are added upstream of the above base sequences and downstream of the stop codons, respectively. A so-called linker can be interposed as in the Experiment described hereinafter. Ordinarily, the structural gene is designed and synthesized to have cohesive ends. [Science, 198, 1056 (1977)]. If desired, both the ends may be blunt-ended.

Generally, the optional base pair to be in front of the ATG codon is 3m pair, (3m+1) pair or (3m+2) pair, in which m is 0 or an integer of at least 1.

A preferred example of the gene for [21-L] hUG suitably used in the present invention, which is designed while taking the above mentioned matters into consideration, is described in the Experiment hereinafter.

(2) Synthesis

Synthesis of the gene designed in the above mentioned manner is accomplished by chemically synthesizing fragments of both the + and − strands and linking these fragments to one another. It is preferable that the two strands of the duplex hUG gene be divided into 26 to 30 fragments each comprising 10 to 17 bases, and the fragments in a given pair are complementarily overlapped through 7 to 10 bases thereof.

As possible processes for the synthesis of the respective fragments, there are the diester method [Science, 203, 614 (1979)], the triester method [Science, 198, 1056 (1977)], the solid phase method [Nucleic Acids Research, 8. 5491 (1980)], the liquid phase method, and the process using an enzyme [J. Biol. Chem., 241, 2014 (1966)]. From the viewpoints of the time for synthesis, yield and purification, the solid phase triester method is most preferred.

Specific conditions for the synthesis are set forth in the above mentioned literature references and the Experiment described hereinafter.

(3) Purification

In the case where an oligonucleotide is chemically synthesized, it ordinarily becomes difficult, with increase of the chain length, to accomplish separation and purification of the final product. Especially in the solid phase method, since appropriately protected oligonucleotide blocks are condensed stepwise, purification cannot easily be accomplished according to a conventional technique such as gel permeation, gel electrophoresis, ion exchange column chromatography or high performance liquid chromatography.

In the reverse phase column chromatography, the retention time is greatly influenced by whether or not the oligonucleotide has one oleophilic protecting group. Accordingly, if an oligonucleotide block having a protecting group which is stable under conditions for removing other protecting groups is used at the final condensation stage, and an appropriate operation is carried out for removing the protecting groups, a mixture of oligonucleotides in which the above protecting group is attached only to the intended final product is obtained. By utilizing the oleophilic property of the above protecting group, the intended final product is separated from the unreacted mixture by the reverse phase column chromatography. Then, the above protecting group is removed, whereby the intended oligonucleotide can be obtained.

According to this process, the synthesized oligonucleotide can be separated and purified from the unreacted mixture.

(4) Phosphorylation and Ligation

The thus synthesized fragments are ligated in sequence by using DNA ligase. In order for the synthetic fragment to be a substrate for this enzyme, it is necessary to phosphorylate the 5'-hydroxyl group of the fragment.

Polynucleotide kinase is ordinarily used for this phosphorylation, but chemical phosphorylation is also possible [Nucleic Acids Research, 8, 5753 (1980)]. DNA ligase is ordinarily used for ligating the fragments, but a process in which 5'-terminal phosphate group is activated by appropriate means (for example, conversion to an imidazole group) and chemical bonding is performed by using the chain of the complementary fragment as a template is also possible [Chem. Pharm. Bull., 26, 2396 (1978)].

(2) Preparation of Vectors Having Lactose Operon

In the present invention, various plasmids comprising all or a part of a lactose operon derived from the E. coli chromosome and being vegetative in the E. coli can be used. These plasmids can be prepared according to conventional procedures known in the field of the molecular biology. Lactose operon-containing DNA can be obtained directly from E. coli chromosome. However, since there are known various transducing phages comprising all or a part of the lactose operon (for example, Pldl, F'-lac, $\phi$80dplac, $\lambda$h80dlac and $\lambda$plac), it is preferable to take up a necessary part of the lactose operon from these phages. In the present invention, in order to form a plasmid vegetative in E. coli, it is necessary to form a recombinant plasmid vector by linking the necessary part of the lactose operon to another plasmid derived from E. coli such as, for example, pBR322, pSC101 or $\lambda$dV1.

As one embodiment in the present invention, transducing phage $\lambda$plac5 [Nature, 224, 768 (1969)] is used as the lactose operon-containing DNA. $\lambda$plac5 DNA can be obtained from E. coli PK1512, which is a $\lambda$plac5 lysogenic bacterium, according to a known process [Extra Number of Proteins, Nucleic Acids and Enzymes, Experiments of Nucleic Acids, Volume II, page 19 (1973)]. This $\lambda$plac5 contains the bacterial chromosomal sequence ranging from the midway of i-gene of the lactose operon to the midway of y-gene and has no bacterial gene other than lactose operon. Therefore, $\lambda$plac5 is preferably used in the present invention. pBR322 is used as the plasmid derived from E. coli. The reasons for selection of this plasmid are that: this plasmid is easily available; all the base sequences have been determined; and it has Ampicillin-resistance and Tetracycline-resistance genes. In order to combine these genes, $\lambda$plac5 and pBR322 are treated with restriction enzymes Eco RI and Hind III; the 3.8 Md fragment derived from $\lambda$plac5 DNA is ligated to the larger fragment of pBR322 to form an expression vector (named "pRE").

The reasons why the lactose operon derived from E. coli chromosome is selected for expression of the intended [21-L] hUG are: that [21-L] hUG gene can be expressed in the form of an insoluble protein fused with $\beta$-galactosidase by insertion at the recognition site for restriction enzyme Eco RI in z-gene in the lactose operon [Science, 198, 1056 (1977)]; that the protein can be produced in a large quantity; that inducible production is possible if an appropriate host bacterium is used; and that the fused protein can be recovered substantially purely and stably from insoluble fractions.

Accordingly, in the present invention, it is preferable that the prepared vector have only one site for recognition of restriction enzyme Eco RI. For this purpose, as described above, $\lambda$plac5 and pBR322 are cleaved by Eco RI and Hind III, respectively, and the cleaved DNA fragments are ligated together.

(3) Recombinant Plasmid

(1) Construction

The above mentioned gene containing the structural gene of [21-L] hUG is inserted at an appropriate site of the vector designed so as to express. The insertion can be accomplished according to conventional procedures known in the field of the molecular biology. A specific process will become apparent from the Experimental Example described hereinafter.

As one example of the present invention, pRE 1 is used as the expression vector, and the gene containing the structural gene of [21-L] hUG is inserted at the Eco RI recognition site of pRE 1 to form a recombinant plasmid. In the present invention, this recombinant plasmid is named "pLE".

(2) Linker

In construction of this recombinant plasmid, both the ends of the gene containing the structural gene of [21-L] hUG may be cohesive ends including the Eco RI recognition site, but in view of future insertion into the recognition site other than the Eco RI recognition site, that is, production of the objective peptide as another fused protein or recombination to another plasmid, it is preferable that the above mentioned ends may be blunt-ended. This example is shown in the Experimental Example described hereinafter. In this example, duplex DNA is necessary as the linker for binding the gene containing the structural gene to pRE 1. That is, this duplex DNA is designed so that it has recognition sites for the two restriction enzymes, Eco RI and Sma I, and the frame beginning with the initiation codon of β-galactosidase is finally in agreement with the reading frame of the structural gene of [21-L] hUG. It is sufficient if this linker finally has the above functions, and the linker can be synthesized according to the same process as the above mentioned process used for the synthesis of the structural gene. In one typical example of the present invention, the linker is prepared according to the following process as an example of this synthesis process.

The following single stranded DNA having the recognition sites for restriction enzymes Eco RI and Sma I is designed:

5'AATTCCCGGG3'

Since this single stranded DNA is self-complementary, it becomes a long duplex DNA having many nicks between two adjacent fragments. The thus obtained duplex DNA is a duplex poly-DNA having recognition sites for restriction enzymes Eco RI and Sma I alternately.

(3) Determining the Orientation of the Gene Insert

The orientation of the [21-L] hUG gene inserted in the plasmid is determined by cleaving the plasmid at the specific site locating in the structural gene by an enzyme (Bgl II) recognizing this site, cleaving the plasmid at a specific position outside the structural gene by another enzyme, and analyzing the size of the obtained fragment.

(4) Transformation (1) Host cell

An example of the host cell to be transformed by using the recombinant plasmid pLE in which the [21-L] hUG structural gene is inserted as described above, for example, pLE 6527, is an *Escherichia coli* strain XA35. The strain XA35 is a derivative of *E. coli*, strain K12, which is a known strain [Microbiological Reviews, 44, 1–56 (1980)]. The properties of the strain XA35 are not different from those of the known strain K12 except for the following properties:

[Sm$^r$, Lac$^-$(i$_3^-$, z)]

The transformation by the plasmid having the [21-L] hUG structural gene inserted therein can be applied to all *E. coli* strains. However, when [21-L] hUG is recovered in the form of a protein fused with β-galactosidase, in order to prevent co-production of normal β-galactosidase, it is preferable that a strain having no β-galactosidase gene be used as the host cell. Ordinarily, production of a protein is controlled by a repressor gene (i-gene) of the lactose operon, but in the case where a wild-type *E. coli* is used, inducible production of a fused protein can be performed by an inducer (such as IPTG), and when a strain whose i-gene product (lactose repressor) is inactivated at a high temperature is used, a fused protein can be formed by elevating the temperature. If a strain of the deficient i-gene is used, a fused protein will constitutively be obtained [The Operon, 31 (1980)].

As one example in the present invention, an *E. coli* strain XA35 of the deleted β-galactosidase gene and the deficient i-gene is used.

(2) Transformation

The transformation can be performed according to conventional procedures known in the field of the molecular biology. A specific process is shown in the Experimental Example described hereinafter.

(3) Transformant

An example of the transformed strain is one obtained by transforming the *E. coli* strain XA 35 by pLE 6527, and in the present invention, this transformed strain is named "*E. coli* XA 35 (pLE 6527)".

As is apparent from the Experimental Example described hereinafter, the transformed *E. coli* XA 35 (pLE 6527) has the same properties as those of the *E. coli* XA 35 except for the following properties:

[Am$^r$, Lac$^+$]

(5) Production of [21-L] hUG

If the transformed strain is cultured according to conventional procedures, [21-L] hUG will be produced. A specific process is shown in the Experimental Example described hereinafter.

EXPERIMENTAL EXAMPLE

Designing of [21-L] hUG gene

Figure 5:
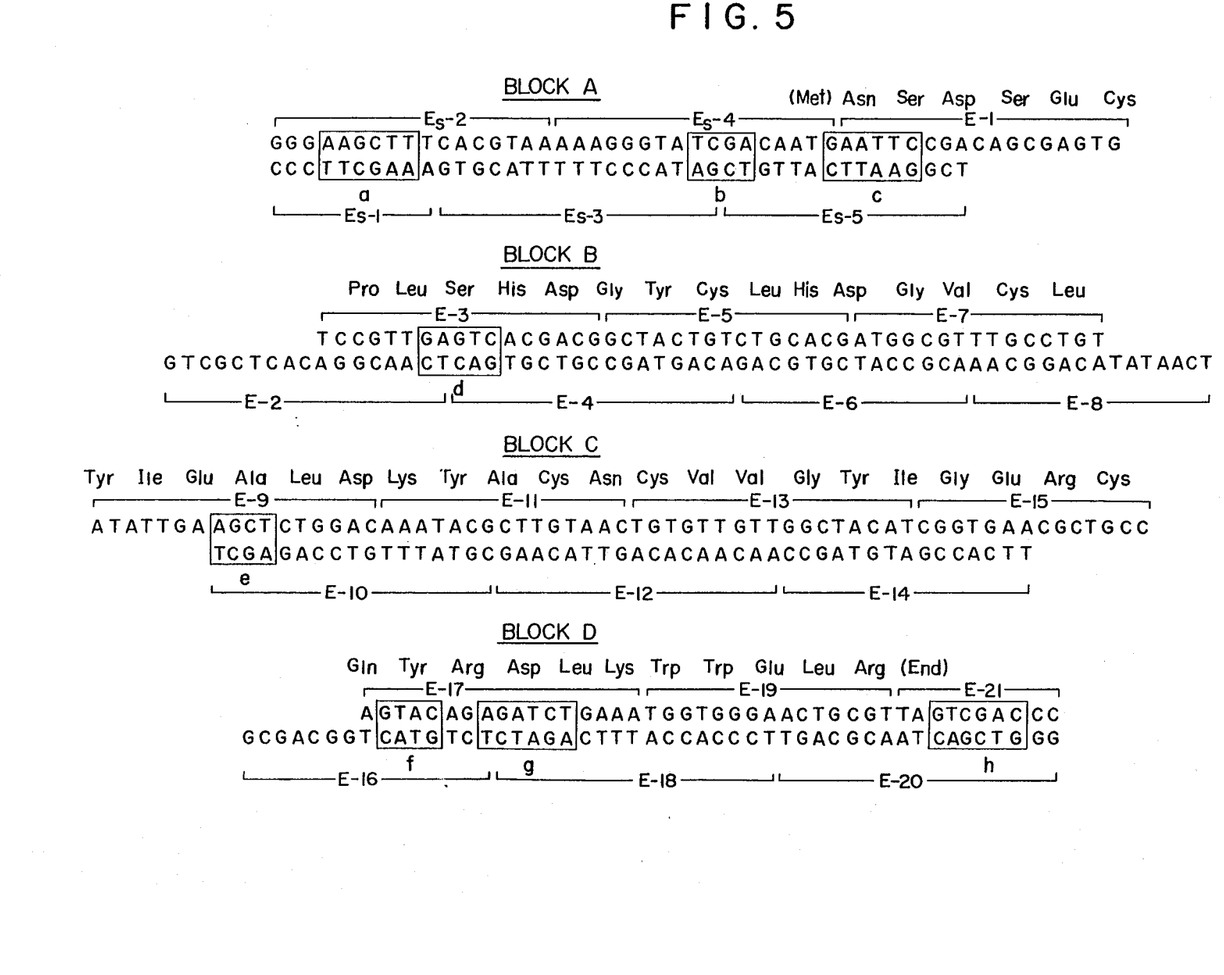
FIG. 5 is a gene design diagram.

As shown in the accompanying gene design diagram, the designed gene was divided into fragments comprising 10 to 17 bases, which were designated as ES1 through ES5 and E1 through E21.

The designing procedure is as follows.

(1) Selection of Codons

Codons are selected as shown in the diagram.

(2) Codon ATG for methionine is added to the N-terminal amino acid of hUG, namely Asn, so that the synthesized polypeptide could be cut at the position by a treatment with CNBr.

(3) One translation termination codon (TAG or TGA) is added to the 3'-terminus of the hUG gene corresponding to the C-terminus so that an additional peptide is not formed.

(4) The 21st amino acid (methionine) is substituted by leucine. The reason for this step is that if methionine is present, cleavage is caused at its carboxyl side by the CNBr treatment, so that an entire hUG cannot be obtained.

(5) For modification of the peptide, base sequences are designed so that one each of restriction enzyme recognition sites Eco RI, HinfI, AluI, RsaI and Bgl II will be located at appropriate positions.

(6) Codons frequently used in the structural genes expressed efficiently in an *E. coli* are used as far as possible.

Chemical Synthesis of Fragments (1) Synthesis

The synthesis of fragments was carried out according to the solid phase method disclosed in literature references, although isolation and purification of the synthesized fragments were performed according to the following improved process.

The synthesis yield of each fragment was 20 to 60%.

| Fragment | Base Sequence | Chain length |
|---|---|---|
| ES 1 | AAAGCTTCCC | (10) |
| ES 2 | GGGAAGCTTTCACGTAA | (17) |
| ES 3 | GATACCCTTTTTACGTG | (17) |
| ES 4 | AAAGGGTATCGACAATG | (17) |
| ES 5 | TCGGAATTCATTGTC | (15) |
| E-1 | AATTCCGACAGCGAGTG | (17) |
| E-2 | TCAACGGACACTCGCTG | (17) |
| E-3 | TCCGTTGAGTCACGACG | (17) |
| E-4 | ACAGTAGCCGTCGTGAC | (17) |
| E-5 | GCTACTGTCTGCACG | (15) |
| E-6 | ACGCCATCGTGCAG | (14) |
| E-7 | ATGGCGTTTGCCTGT | (15) |
| E-8 | TCAATATACAGGCAA | (15) |
| E-9 | ATATTGAAGCTCTGGAC | (17) |
| E-10 | CGTATTTGTCCAGAGCT | (17) |
| E-11 | AAATACGCTTGTAAC | (15) |
| E-12 | AACAACACAGTTACAAG | (17) |
| E-13 | TGTGTTGTTGGCTACAT | (17) |
| E-14 | TTCACCGATGTAGCC | (15) |
| E-15 | CGGTGAACGCTGCC | (14) |
| E-16 | TCTGTACTGGCAGCG | (15) |
| E-17 | AGTACAGAGATCTGAAA | (17) |
| E-18 | TCCCACCATTTCAGATC | (17) |
| E-19 | TGGTGGGAACTGCGT | (15) |
| E-20 | GGGTCGACTAACGCAGT | (17) |
| E-21 | TAGTCGACCC | (10) |

(2) Purification

To 20 mg of the synthetic resin were added 0.5M α-picoline-aldoxime tetramethylguanidine and 200 μl of a 1/1 mixture of dioxane/water, and the mixture was allowed to stand at room temperature overnight, and then 2 ml of concentrated aqueous ammonia was added to the mixture. The reaction vessel was plugged, and the mixture was allowed to stand at 55° C. overnight. The mixture was filtered to separate the resin, and the filtrate was concentrated and subjected to gel filtration. Elution was carried out with 50 mM TEAB buffer solution (pH 7.5) and the eluate in a void volume was collected and concentrated. The concentrate was subjected to HPLC using a reverse phase column C-18 [Radial Pack A supplied by Waters Co.; 8 cm (diameter)×10 cm (length)], and elution was carried out at a flow rate of 2 ml/min over a period of 16 minutes with a linear gradient of 10%–32% acetonitrile in 0.01M ethylene diamine diacetate buffer solution (pH 7.8).

The fraction eluted between 11 and 12 minutes after the start of elution was collected. At this time, an oligonucleotide having no trityl group was eluted as an injection peak. The eluate was concentrated, and 1 ml of 80% acetic acid was added and the mixture was allowed to stand at room temperature for 15 minutes. Tritanol was removed by extraction, and the aqueous layer was concentrated and subjected to reverse phase column chromatography again. Under the same conditions as described above, elution was carried out with a linear gradient of 0% to 20% acetonitrile, and the fraction eluted between 12 and 13 minutes (that is, a fragment) was collected. Then, 10 pmol (0.001 $A_{260}$) of this fragment was dissolved in a mixture of 20 mM trishydrochloric acid buffer solution (pH 7.5), 10 mM $MgCl_2$, 10 mM DTT and 0.5 mM ATP, and 10 μci (3.3 pmol) of [$\gamma^{32}P$]ATP and 1 μl (4.5 units) of $T_4$-polyhucleotide kinase were added to the solution so that the total volume was 20 μl. The mixture was heated at 37° C. for 20 minutes and at 100° C. for 2 minutes to stop the reaction.

The purity of the fragment was checked by 20% polyacrylamide gel electrophoreses and the correct base sequences were examined by two-dimensional homochromatography [Nucl. Acids Res., 1, 331 (1974) and Nucl. Acids Res., 6, 2069 (1979)].

Ligation of the Fragments

The synthesized fragments were divided into the following four blocks and subjected to ligation reaction.

| Block | Fragment |
|---|---|
| A | Es - 1, Es - 2, Es - 3, Es - 4, Es - 5, E - 1 |
| B | E - 2, E - 3, E - 4, E - 5, E - 6, E - 7, E - 8 |
| C | E - 9, E - 10, E - 11, E - 12, E - 13, E - 14, E - 15 |
| D | E - 16, E - 17, E - 18, E - 19, E - 20, E - 21 |

In the case of block A, 100 pmol (0.01 $A_{260}$) each of Es - 1, Es -2, Es - 3, Es -4, Es -5 and E - 1 were dissolved in a mixture of 20 mM tris-hydrochloric acid buffer solution (pH 7.5), 10 mM $MgCl_2$, 10 mM DTT, and 0.5 mM ATP so that the total volume was 50 μl, and $T_4$-polynucleotide kinase (8 units) was added. Reaction was carried out at 37° C. for 1 hour. Then, phosphorylation was carried out, and $T_4$-DNA ligase (900 units) was added. Ligation reaction was thus carried out at 14° C. for one night to obtain block A. Other blocks B - D were obtained according to the same procedure as described above with respect to block A.

Block A was mixed with the reaction mixture of block B, and, with the addition of 1/10 by volume of 0.5 mM ATP and $T_4$-DNA ligase (900 units), and reaction was carried out overnight at 14° C. Then, 1/10 by volume of 3M sodium acetate (pH 5.5) was added to the reaction mixture, and three times volume of ethanol was added to the mixture. The resultant mixture was cooled at −70° C. for 15 minutes and subjected to centrifugation at 12,000 rpm to obtain a precipitate. The precipitate was subjected to 10% polyacrylamide gel electrophoresis to separate the ligated block [A+B]. A band corresponding to the block [A+B] was cut out, and then the fragment [A+B] was purified by electrophoresis in a 1.5% low-melting-point agarose gel. Similar operations were applied to blocks C and D to form the block [C+D].

The thus obtained blocks [A+B] and [C+D] were mixed in a ratio of 1:1, and ligation of the two blocks was carried out in the same manner as described above. The reaction mixture obtained was subjected to precipitation with ethanol to obtain a highly polymerized gene DNA. The precipitate was dissolved in a mixture of 10 mM tris-hydrochloric acid buffer solution (having a pH value of 8.0), 7 mM $MgCl_2$ and 20 mM KCl, and reaction was carried out at 37° C. for 1 hour with Sma I (5 units). To the reaction mixture was added a mixture of one-tenth volume of 100 mM tris-hydrochloric acid buffer solution (pH 8.0), 70 mM of $MgCl_2$ and 600 mM NaCl, and the mixture was incubated at 37° C. for 1 hour with Hinc II (50 units), whereby an objective gene having a chain length of 198 base pairs and containing Sma I and Hinc II at both the ends was obtained. Then, 8% polyacrylamide gel electrophoresis was carried out, and the gene was recovered according to the same procedure as described above.

Preparation of pREl

10 μg of λplac5 DNA (Japanese Patent Application No.16734/82) was added to a mixture (the total volume being 20 μl) of 100 mM tris-hydrochloric acid buffer solution (pH 7.5), 7 mM $MgCl_2$ and 50 mM NaCl, and reaction was carried out at 37° C. for 2 hours with 10 units of restriction enzyme Eco RI and 10 units of restriction enzyme Hind III. Then, 3.8 Md fragment was purified by 1% agarose gel electrophoresis.

1 μg of pBR 322 DNA was added to the same mixture as described above (the total volume being 10 μl), and reaction was carried out at 37° C. for 2 hours with 1 unit of restriction enzyme Eco RI and 1 unit of restriction enzyme Hind III. Then, a DNA fragment of 2.6 Md was purified by 1% agarose gel electrophoresis.

The fragments thus obtained were added to a mixture (the total volume being 10 μl) of 50 mM trishydrochloric acid buffer solution (pH 7.8), 10 mM $MgCl_2$, 20 mM DTT and 1 mM ATP, and reaction was carried out at 14° C. for 24 hours with 30 units of $T_4$-DNA ligase.

Transformation of *E. coli* strain XA 35 was performed by using the reaction mixture thus obtained according to the Kuschner's method [see Genetic Engineering, 1978, 17 (1978)]. The experiment was performed in P-1 physical confinement equipment (Guide to Recombination DNA Experiments).

The transformed strains were selected on an L-plate (1% bactotryptone, 0.5% bactoyeast extract, 0.5% NaCl and 1.5% bactoagar) containing Ap (20 μg/ml), and the transformed strains obtained were replica-plated on an EMB-lac plate (2.25% bacto-EMB-brose, 1.5% bactoagar). The strains of Lac+ (red colony) were further selected, and five strains were chosen among these strains and used for the preparation of plasmids. On the basis of the data of restriction analysis, it was confirmed that in the plasmids of the four strains, the λplac5 DNA fragment of 3.8 Md was ligated to the Eco RI-Hind III fragment of pBR 322 DNA. One of these strains was named "*E. coli* XA 35 (pREl)". This transformed *E. coli* XA 35 (pRE 1) was different from the above mentioned *E. coli* XA 35 for the following properties:

[$Am^r$, $Lac^+$]

Construction of pRS 23 pRE 1 (30 μg) was added to a mixture of 100 ml of tris-hydrochloric acid buffer solution (pH 7.5), 7 mM $MgCl_2$ and 50 mM NaCl, and reaction was carried out at 37° C. for 1 hour with restriction enzyme Eco RI (4 units), after which reaction was further continued at 37° C. for 30 minutes in the presence of 5 units of bacterial alkaline phosphatase. After completion of the reaction, the reaction mixture was extracted twice with an equal volume of phenol (saturated with a mixture of 10 mM trishydrochloric acid and 1 mM EDTA, pH 8.0), and precipitation with ethanol was then carried out. The precipitate obtained was dissolved in a mixture of 20 mM trishydrochloric acid buffer solution (pH 7.5), 10 mM $MgCl_2$, 5 mM DTT and 0.5 mM ATP, and the solution was mixed with 2-fold volume of the Eco RI-Sma I linker (AATTCCCGGG), after which reaction was carried out at 14° C. overnight with $T_4$-DNA ligase (300 units). Transformation of *E. coli* XA 35 was performed using the reaction mixture obtained according to the Kuschner's method [Genetic Engineering 1978, 17 (1978)]. The transformed strains were selected on an L-plate containing Ampicillin (20 μg/ml), and the transformed strains were replica-plated on an EMB-lac plate. Then strains of Lac+, Amp+ were further chosen. Plasmid DNA to be cut by restriction enzymes Sma I and Eco RI was obtained from these strains and designated as "pRS 23 ".

Construction of pLE 6527 and its Cloning pRS 23 (6.8 μg) was incubated with restriction enzyme Sma I (50 units) at 37° C. for 1 hour in 10 mM trishydrochloric acid buffer solution (pH 8.0), 7 mM $MgCl_2$ and 20 mM KCl.

Then, bacterial alkaline phosphatase (5 units) was added to the reaction mixture, and reaction was carried out at 42° C. for 30 minutes. After completion of the reaction, the reaction mixture was extracted with phenol, similarly as described above, and precipitation with ethanol was carried out. The precipitate was dissolved in 20 mM tris-hydrochloric acid buffer solution (pH 7.5), 10 mM $MgCl_2$, 5 mM DTT and 0.5 mM ATP, and [21-L] hUG gene segment (6 pmol) was added to the solution. Thus reaction was carried out at 14° C. overnight with $T_4$-DNA ligase (1800 units). Transformation of *E. coli* XA 35 was carried out using the reaction mixture in the same manner as described above (the Kuschner's method), and transformed strains (resistant to Ampicillin) were selected. Plasmid DNA was prepared from these strains, and plasmid strains to be cut by restriction enzyme Bgl II were chosen. If a structural gene of EGF is inserted in the plasmid, it has a recognition site for this restriction enzyme, and hence, a marker for selection of the intended plasmid is obtained. In order to confirm the orientation of the inserted gene segment, the Hind III-Pst I treatment was carried out to select a plasmid strain thought to have a correctly inserted hUG gene segment.

Then, plasmid DNA was prepared from this strain, on the basis of results of restriction analysis with Hind III and Hinc II, it was confirmed that a fragment of 141 base pairs was generated. This fragment (fragment of 141 base pairs generated by Hind III-Hinc II) was cloned to the Hind III-Hinc II site of phage M-13mp8, and the sequences were examined by the dideoxy sequencing method [Sanger method; Proc. Natl. Acad. Sci. USA, 74, 5463 (1977)]. Thus it was confirmed again that the gene was inserted with the correct orientation.

Culturing of the transformed Cells

*E. coli* XA 35 (pLE 6527), which contained the recombinant plasmid pLE 6527 having the [21-L] hUG gene inserted therein, was cultured at 37° C. for 4.5 hours with aeration in a Luria medium (1% bactotrypton, 0.5% bacto-yeast extract and 0.5% NaCl) to which 0.4% glycerol and 20 μg/ml of Ampicillin were added, and culturing was continued to the late logarithmic phase or early stationary phase ($A_{600}=1.4$). Then, cells were collected by centrifugation and washed twice with 170 ml of 10 mM tris-hydrochloric acid buffer solution (pH 8), 10 mM $MgCl_2$ and 5 mM β-mercaptoethanol. Finally, 32.6 g (wet weight) of cells were obtained by the above operations.

Partial Purification of [21-L] hUG 32.6 g of the cells were suspended in 140 ml of 10 mM tris-hydrochloric acid buffer solution (pH 8), 1 mM $MgCl_2$, 1 mM PMSF (phenylmethylsulfonyl fluoride) and 5 mM β-mercaptoethanol, and the cells were pulverized under ice cooling by ultrasonic treatment using an Insonator 200M (Kubota). The thus obtained bacterial lysates were subjected to centrifugation at 27,000 g for 30 minutes, and pellets were collected and washed twice with 120 ml of 10 mM tris-hydrochloric acid buffer solution (pH 8), 10 mM $MgCl_2$, 1 mM PMSF and 5 mM β-mercaptoethanol. The pellets were stirred at 4° C. overnight in 150 ml of 50 mM tris-hydrochloric acid buffer solution containing 8M guanidine, 1 mM EDTA and 5 mM 8-mercaptoethanol and the resultant suspension was dialyzed against water. The precipitates formed by dialysis were collected by centrifugation at 65,000 g for 30 minutes and were re-suspended in 100 ml of 20 mM tris-hydrochloric acid buffer solution (pH 8) containing 7M urea, 1 mM $MgCl_2$ and 5 mM β-mercaptoethanol, and centrifugation was done again at 27,000 g for 30 minutes to obtain supernatants. By SDS gel electrophoresis, it was confirmed that the fused protein of β-galactosidase and [21-L] hUG was recovered in this supernatant, and from the results of quantification of the protein content, it was estimated that the amount of protein was 2.66 g.

The supernatant containing the fused protein of [21-L] hUG (in an amount corresponding to 1 g of the protein) was applied to a DEAE-cellulose column equilibriated with 20 mM tris-hydrochloric acid buffer solution (pH 8), 1 mM $MgCl_2$, 5 mM β-mercaptoethanol and 50 mM NaCl and the column was washed with 60 ml of the above mentioned buffer to remove the non-adsorbed protein. Then, the sodium chloride concentration was linearly elevated from 50 mM to 300 mM (a linear concentration gradient with 500 ml each of buffer solutions containing 50 mM and 300 mM sodium chloride, respectively) to elute the [21-L] hUG-fused protein. The fraction containing the fused protein was collected and dialyzed to remove urea and insolubilize the protein and the protein was collected by centrifugation (65,000 g, 30 minutes). Then, the partially purified fused protein (143 mg) thus obtained was dissolved in 70 ml of 70% formic acid, and 1.8 g of cyanogen bromide was added, after which reaction was carried out with shaking at room temperature for 20 hours. The reaction mixture was concentrated by means of an evaporator, and, after 50 ml of distilled water was added to the concentrate, freeze drying was done to remove completely formic acid, unreacted cyanogen bromide, methyl cyanide formed as a by-product and hydrogen bromide. The residue obtained by the cyanogen bromide treatment was extracted with water and dialyzed to obtain 14.1 mg of peptides.

Identification and Bioassay of [21-L] hUG

It has been elucidated that a receptor which binds specifically to mouse EGF (mEGF) and h/EGF/hUG is present on the surface of a cell membrane of cornea cell, human fibroblast, human epidermoid carcinoma cell, mouse 3T3 cell or human chorionic cell. It is reported that EGF binds to the receptor on the membrane surface and is taken into the cell in the form of a complex with the receptor by endocytosis to exert various physiological actions such as promotion of proliferation and differentiation of epithelial cells and fibroblasts, induction of precocious eyelid-opening and incisor eruption in the newborn mouse, inhibition of gastric acid secretion, promotion of biosyntheses of DNA and proteins and promotion of transport of potassium ion and deoxyglucose and transport of low-molecular-weight substances [Ann. Rev. Biochem., 48, 193 (1979)]. Identification and bioassay of [21-L] hUG were done on the basis of this knowledge.

(1) Radioreceptor Assay (RRA)

RRA of [21-L] hUG was carried out using KB cells (ATCC No. CCL17) derived from a human nasopharyngeal epidermoid carcinoma in the light of the process of A. King et al [see J.B.C., 257, 3053 (1982)]. More specifically, monolayer culturing was carried out in DME medium in a 800-ml flask. The culture medium was removed, and cells were peeled with a phosphate buffer salt solution (PBS) containing 0.05% of EDTA to prepare a cell suspension. Then, the cells were washed 2 times with Hank's balanced salt solution (HBSS) containing 20 mM Hepes (pH 7.4). Then, the cells were suspended in a binding solution (DME medium, 20 mM Hepes, pH 7.4, 0.35 g/l of $NaHCO_3$ and 100 μg/ml of Streptomycin), and the cell number was calculated and the cell density was adjusted to from 300,000 to 400,000 per 0.2 ml of the binding solution. The suspension was poured into tubes (0.2 ml in each tube), and 0.2 ml each of sample containing [21-L] hUG and $^{125}I$-mEGF (mouse EGF) at various concentrations were added into the tubes, respectively. Incubation was carried out at 37° C. for 1 hour. The cells were washed 3 times with ice-cold HBSS and suspended in 10% TCA, and the cells were separated from the solution by filtration through a glass filter. TCA was removed with acetone, and counting of radioactivity associated with the cells was performed by using a scintillation counter.

Figure 1:
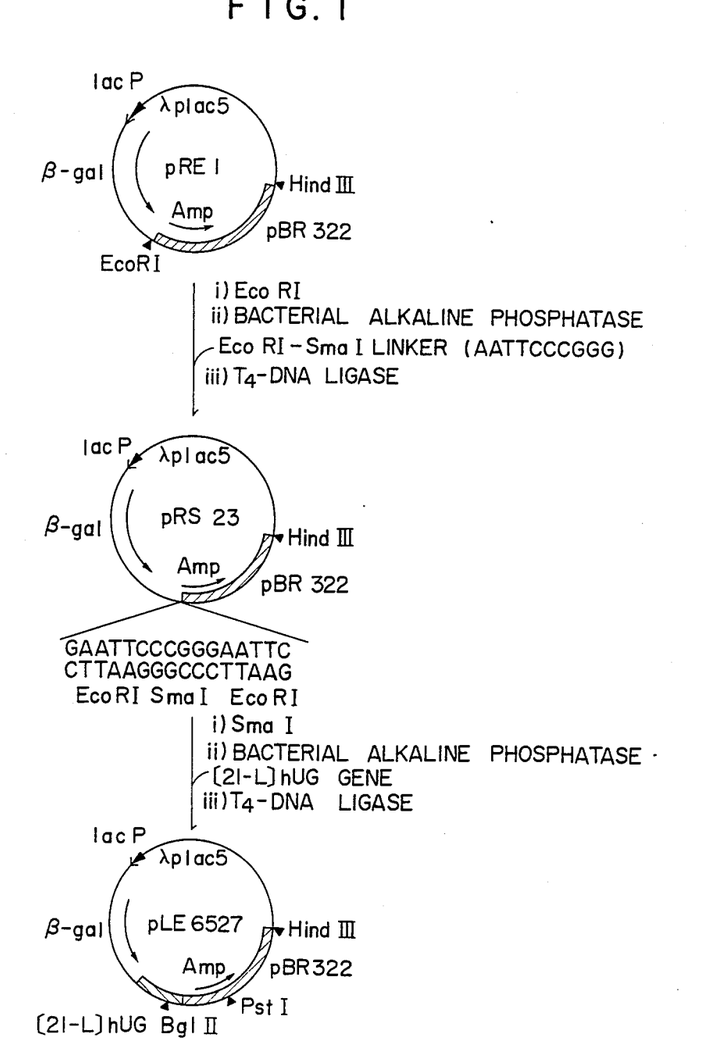
FIG. 1 is a diagram showing the construction of a recombinant plasmid containing the structural gene of [21-L] hUG.
Figure 2:
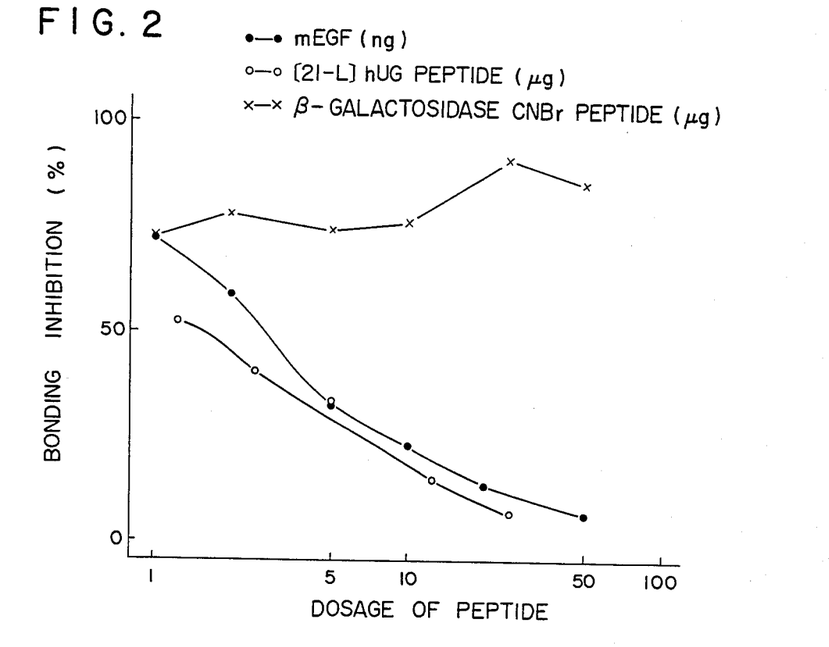
FIG. 2 is a graph indicating the results of RRA.

For comparison, mEGF (Toyobo, Japan) and a peptide fraction obtained by the cyanogen bromide treatment of β-galactosidase were similarly tested. The results obtained are shown in FIG. 2. As is apparent from FIG. 2, the peptide fraction comprising [21-L] hUG competitively inhibits binding of $^{125}I$-mEGF to the KB cell EGF receptor, and its dosage-response curve is in good agreement with that of mEGF.

RPA using mouse 3T3 cell was carried out according to the process of C. Savage et al [Anal. Biochem., 111, 195 (1981)], and results similar to the results obtained in RRA using KB cell were obtained.

Figure 3:
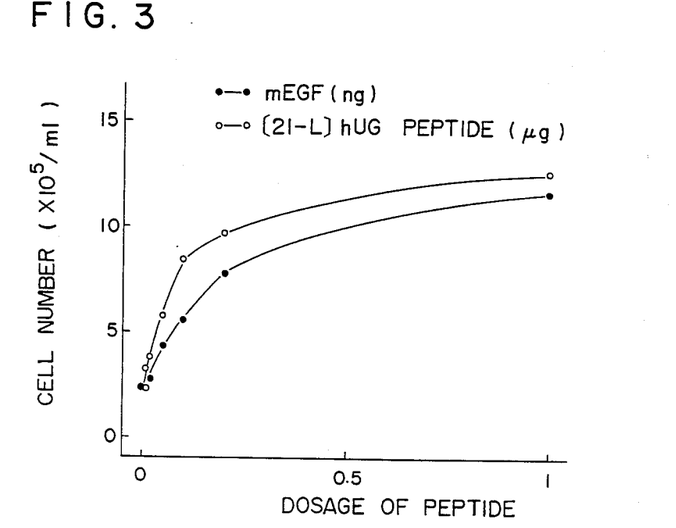
FIG. 3 is a graph indicating the activity of stimulation of cell proliferation.

(2) Bioassay based on the Activity of Promoting Proliferation of Mouse 3T3 Cell as an Indicator The activity of promoting proliferation of cells was determined by the following procedure. More specifically, monolayer culturing of mouse 3T3 cells was carried out in a 25-$cm^2$ flask, and the cells were treated with calcium- and magnesium-free HBSS (CMF-HBSS) containing 0.02% of EDTA and 0.05% of trypsin to prepare cell suspensions. The cells were washed with CMF-HBSS and resuspended in DME medium containing 0.5% of fetal bovine serum (FBS), and the number of viable cells was counted. The cell suspension was diluted with 0.5% FBS-DME medium so that the cell number was $2\times10^4$ per ml. Then, 1 ml of the cell suspension was seeded per 35 mm dish and incubation was carried out overnight in a $CO_2$ incubator. Peptide fractions containing different concentrations of [21-L] hUG and mEGF as a control were dissolved in 0.5% FBS-DME medium and the mixtures were filtered by a Millipore filter (type GV, wpo 2500), and 1 ml aliquots of the mixtures were added to the above cell suspension. Incubation was carried out for 4 days in a $CO_2$ incubator (5% $CO_2$-95% air, 37° C.). Viable cells were stained with Trypan Blue, and the number of the viable cells was counted using a counting chamber. The results obtained are shown in FIG. 3. The obtained dose-response curve was in good agreement with the curve for mEGF. The peptide fraction obtained by cyanogen bromide treatment of β-galactosidase as a control had no proliferation-promoting activity.

(3) Bioassay of Activity stimulating Thymidine Incorporation

Incorporation of thymidine was determined according to a modification of the method of Aharon Aharonov et al [J.B.C., 253, 3970 (1978)] and the method of Jimenez de Asua et al [PNAS, 72, 2724 (1975)]. More specifically, $6\times10^3$ of mouse 3T3 cells were seeded in 0.5 ml of 5% FBS-DME medium in a multi-well dish, and culturing was done for 5 days to grow as monolayers to sub-confluency. The medium was removed, and the cells were washed with PBS, and 0.5 ml of 0.5% FBS-DME medium was added. Incubation was done overnight. Then, 0.5 ml of 0.5% FBS-DME medium containing [21-L] hUG at a predetermined concentration or mEGF was added, and incubation was further continued for 18 hours. Then, 200 nci of [$^3$H]-thymidine was added, and incubation was carried out at 55° C. for 30 minutes. The cells were washed twice with cold HBSS containing 20 mM Hepes (pH 7.4) and washed twice with 5% TCA. Then, 200 μl of 1N NaOH was added, and incubation was carried out at 55° C. for 30 minutes to dissolve DNA. Then, 50 μl of the DNA solution was taken and 25 μl of 2N HCl was added for neutralization. The radio-activity of Thymidine was measured by means of a liquid scintillation counter. The obtained results are shown in the following Table.

|  | $^3$H—Thymidine cpm | In-take Amount Δcpm |
|---|---|---|
| No addition | 4,639.5 |  |
| mEGF |  |  |
| 10 ng/ml | 14,094.6 | 9,455.1 |
| 5 ng/ml | 14,695.2 | 10,055.7 |
| 2 ng/ml | 13,387.4 | 8,747.9 |
| 1 ng/ml | 14,510.5 | 9,871.0 |
| [21-L] hUG peptide |  |  |
| 2.93 μg/ml | 13,567.0 | 8,927.5 |
| 1.46 μg/ml | 11,761.7 | 7,122.2 |
| 0.73 μg/ml | 17,170.8 | 12,531.3 |

As is apparent from the results shown in the above Table, the [21-L] hUG peptide fraction promotes greatly thymidine incorporation.

(4) Purification and Identification of [21-L] hUG by High Performance Liquid Chromatography (HPLC)

The peptide fraction containing [21-L] hUG and the peptide fraction obtained from *E. coli* XA 35 (pREl) containing only the vector plasmid with no [21-L] hUG gene being inserted, which were prepared by the same treatment as described above, were analyzed by HPLC using a μ-bonda pack C-18 column (0.4 cm×30 cm, Waters Co.) while the acetonitrile concentration in 0.1 trifluoroacetic acid (TFA) was increased at a rate of 0.75%/min at 50° C. and a flow rate of 2 ml/min.

Figure 4:
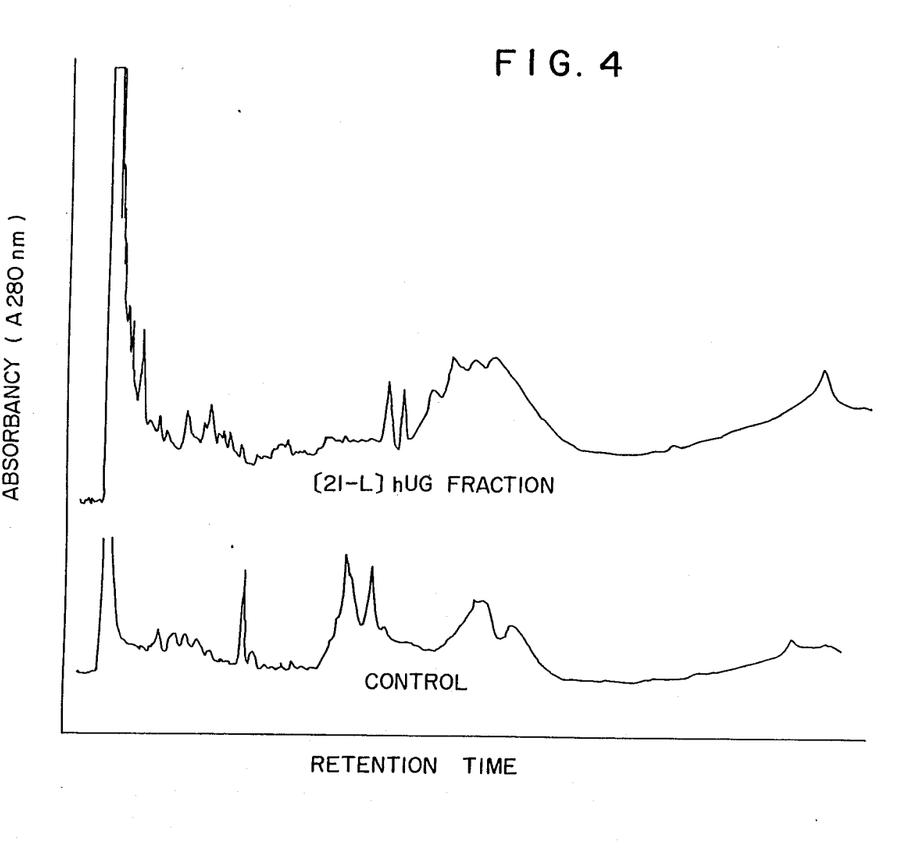
FIG. 4 is a graph showing an elution profile of the [21-L] hUG fraction by reverse phase HPLC.

The obtained elution pattern is shown in FIG. 4. As is seen from FIG. 4, two peaks (retention times of 18.4 minutes and 19.3 minutes) were observed in the peptide fraction containing [21-L] hUG, but these peaks were not found in the peptide fraction obtained from *E. coli* XA 35 (pREl). The above fractions were separated and subjected to RRA and the bioassay for the activity of promoting proliferation of 3T3 cells. The activity was observed in the both fractions. In view of the difference of the retention time, it was presumed that the above two peaks are [21-L] hUG having a complete structure and [21-L] hUG$_{1-51}$ lacking Arg and Leu at the C-terminus or [21-L] hUG$_{1-48}$ lacking the C-terminal 5 amino acids, respectively. [Anal. Biochem., 111, 195 (1981) and J.B.C., 247, 7609 (1972)].

From the foregoing results, it has been confirmed that [21-L] hUG can be purified according to reverse phase HPLC.

More particularly, the [21-L] hUG obtained in FIG. 4 was subjected further to reverse-phase HPLC to obtain a fraction (one peak), and the amino acid contents of the fraction were determined by hydrolysis thereof by 6N HCl and then by amino acid analysis. The fraction obtained from the reverse phase HPLC also gave one band upon electrophoresis. The amino acid sequence determined is as follows.

| | Amino acid contents | | |
|---|---|---|---|
| | nmole | Converted, Asp being 7.0 | Rounded | Theoretical |
| Asp | 1.78 | 7.0 | 7 | 7 |
| Thr | — | — | — | — |
| Ser | 0.63 | 2.5 | 3 | 3 |
| Glu | 1.35 | 5.3 | 5 | 5 |
| Pro | 0.33 | 1.3 | 1 | 1 |
| Gly | 0.92 | 3.6 | 4 | 4 |
| Ala | 0.55 | 2.2 | 2 | 2 |
| Cystin | 1.04* | 2.6 | 3 | 3 |
| Val | 0.64 | 2.5 | 3 | 3 |
| Met | — | — | — | — |
| Ile | 0.44 | 1.7 | 2 | 2 |
| Leu | 1.52 | 6.0 | 6 | 6 |
| Tyr | 1.31 | 5.2 | 5 | 5 |
| Phe | — | — | — | —. |
| His | 0.53 | 2.1 | 2 | 2 |
| Lys | 0.46 | 1.8 | 2 | 2 |
| Trp | 0.80** | 1.5 | 2 | 2 |
| Arg | 0.73 | 2.9 | 3 | 3 |
| total amino acids | | | 53 | 53 |

*The data was obtained on cysteic acid obtained upon oxidation of the cystin (hydrolysis by 6 N HCl).
**The data was obtained upon hydrolysis of [21-L] hUG by 30% thioglycollic acid and 5.8 N HCl.

Further, analysis of the amino acid sequence at the C-terminus by means of Carboxy peptidase W (SEIKAGAKU KOGYO Co., Ltd., Japan) gave the following data, whereby it was affirmed that the amino acid sequence is:

$^{48}$-Lys-Trp-Trp-Glu-Leu-$^{53}$Arg-OH

| Amount of amino acids released by the action of Carboxy peptidase W | | | | | | | |
|---|---|---|---|---|---|---|---|
| Standard Amino Acids | | Reaction: 0.5 hr | | Reaction: 3.0 hrs. | | Reaction: 15.0 hrs | |
| | N—Leu ratio | pmole | N—Leu ratio | pmole | N—Leu ratio | pmole | N—Leu ratio | pmole |
| Glu | 1.40 | 1000 | 0.04 | 30 | 0.23 | 170 | 0.24 | 170 |
| Leu | 1.10 | 1000 | 0.05 | 40 | 0.19 | 180 | 0.21 | 190 |
| Lys | 1.80 | 1000 | — | — | 0.08 | 40 | 0.22 | 120 |
| Trp | 0.40 | 1000 | — | — | 0.08 | 190 | 0.13 | 330 |
| Arg | 0.80 | 1000 | 0.11 | 130 | 0.14 | 180 | 0.15 | 190 |

Still further, analysis of the amino acid sequence at the N-terminus by means of a vapor-phase protein sequencer (Applied Biosystems 470A Protein Sequencer) showed that the sequence is:

The symbol "( )" in the sequence shows that no determination of amino acids was possible possibly because the amino acids at 2-, 4-, and 9- positions corresponded to Ser, and the amino acids at 6-, 14- and 20- positions corresponded to Cystein.

Accordingly, [21-L] hUG was thus identified by the experimental results given hereinabove, and it has thus been affirmed that [21-L] hUG was actually produced.

Inhibitory Effect of [21-L] hUG on Generation of Stomach Ulcer

The inhibitory effect of [21-L] hUG on generation of ulcer was examined on the basis of the activity of EGF of anti-gastric acid secretion [Gut, 16, 887 (1975)].

7-weeks-old male rats of the Wister strain were bred and caused to fast for 24 hours before ligation of the pylorus. The pylorus was ligated for 17 hours, and ulcer was caused by fasting and abstinence from drinking. The peptide fraction containing [21-L] hUG (corresponding to 500 μg of the protein) or physiological saline as a control was hypodermically injected 30 minutes before ligation of the pylorus. Each group tested consisted of 5 rats, and the anti-ulcer action was evaluated by calculating the ulcer index. More specifically, the long and short diameters of the olcerous erosion generated by ligation of the pylorus were measured under an anatomical microscope, and the sum of products of the long and short diameters per rat was defined as the ulcer coefficient.

The obtained results are shown in the following Table.

| | Ulcer Coefficient (mm²) |
|---|---|
| [21-L] hUG | 44.5 ± 18.0 |
| Control (physiological saline) | 79.5 ± 15.1 |

The results shown in the Table indicate that the [21-L] hUG fraction tends to inhibit generation of the ulcer.

On the basis of the results described above, it is confirmed that [21-L] hUG has physiological activities equivalent to those of natural hUG and mEGF. From these results, also, it is virtually confirmed that [21-L] hUG obtained according to the present invention has three disulfide bonds at the same positions as in natural hUG or mEGF. That is, the three disulfide bonds are indispensable for the physiological activities of these physiologically potent peptides. As is taught in Ann. Rev. Biochem., 48, 193–216 (1979) and J. Biol. Chem., 247, 5928 (1972), if the disulfide bonds are reduced in mEGF, the activities are completely lost, and, if oxidation is then performed, the activities are restored according to the degree of the oxidation.

Gene Design Diagram

FIG. 5 shows amino acid sequences of [21-L] hUG and base sequences of the gene segment containing the structural gene thereof, which are divided into blocks A, B, C and D.

a: Hind III site, b: Tag I site, c: Eco RI site,
 d: Hinf I site, e: Alu I site, f: Rsa I site,
 g: Bgl II site, h: Hinc II site

| Microorganisms Used and Deposit Numbers | | |
|---|---|---|
| Microorganism | Deposit Number | Receipt Date |
| E. coli K12C600 | FERM BP-115 | June 9, 1981 |
| E. coli K12C600 (pBR322) | FERM BP-235 | June 9, 1981 |
| E. coli XA35 | FERM BP-116 | January 7, 1982 |
| E. coli XA35 (pRE1) | FERM BP-117 | January 7, 1982 |
| E. coli XA35 (pLE6527) | FERM BP-514 | July 2, 1983 |
| E. coli PK1512 | ATCC 39044 | February 8, 1982 |

What is claimed is:

1. (21-Leucine)-human urogastrone comprising a polypeptide represented by the following amino acid sequence:

said (21-leucine) human urogastrone possessing the biological activity of human urogastrone.

2. A pair of complimentary strands of polydeoxyribonucleotide comprising a structural gene capable of expressing (21-leucine) human urogastrone having the biological activity of human urogastrone.

3. A pair of complementary strands of polydeoxyribonucleotide as set forth in claim 2, wherein the structural gene is represented by the following base sequence formula:

```
Asn   Ser   Asp   Ser   Glu   Cys
AAT—TCC—GAC—AGC—GAG—TGT—
TTA—AGG—CTG—TCG—CTC—ACA—
```

-continued

```
Pro  Leu  Ser  His  Asp  Gly
CCG—TTG—AGT—CAC—GAC—GGC—
GGC—AAC—TCA—GTG—CTG—CCG—

Tyr  Cys  Leu  His  Asp  Gly
TAC—TGT—CTG—CAC—GAT—GGC—
ATG—ACA—GAC—GTG—CTA—CCG—

Val  Cys  Leu  Tyr  Ile  Glu
GTT—TGC—CTG—TAT—ATT—GAA—
CAA—ACG—GAC—ATA—TAA—CTT—

Ala  Leu  Asp  Lys  Tyr  Ala
GCT—CTG—GAC—AAA—TAC—GCT—
CGA—GAC—CTG—TTT—ATG—CGA—

Cys  Asn  Cys  Val  Val  Gly
TGT—AAC—TGT—GTT—GTT—GGC—
ACA—TTG—ACA—CAA—CAA—CCG—

Tyr  Ile  Gly  Glu  Arg  Cys
TAC—ATC—GGT—GAA—CGC—TGC—
ATG—TAG—CCA—CTT—GCG—ACG—
```

-continued

```
Gln  Tyr  Arg  Asp  Leu  Lys
CAG—TAC—AGA—GAT—CTG—AAA—
GTC—ATG—TCT—CTA—GAC—TTT—

Trp  Trp  Glu  Leu  Arg
TGG—TGG—GAA—CTG—CGT
ACC—ACC—CTT—GAC—GCA
```

4. A pair of complementary strand of polydeoxyribonucleotide as set forth in claim 2, wherein the 5'-terminus of the structural gene contains a codon for methionine and the 3'-terminus of the structural gene contains at least one stop codon.

5. A recombinant plasmid containing a structural gene capable of expressing (21-leucine) human urogastrone having the biological activity of human urogastrone.

6. An *E. coli* which has been transformed by recombinant plasmid capable of proliferation in a predetermined host cell, which recombinant plasmid is integrated with a chemically synthesized structural gene capable of expressing (21-leucine) human urogastrone corresponding to polypeptide in which the 21st amino acid of human urogastrone is leucine, said (21-leucine) human urogastrone having the biological activity of human urogastrone.

* * * * *